United States Patent [19]

Kaneko

[11] Patent Number: 4,575,808
[45] Date of Patent: Mar. 11, 1986

[54] METHOD OF RECORDING DENSITOGRAM REPRESENTING DENSITIES OF FRACTIONATED SUBSTANCES

[75] Inventor: Nobutaka Kaneko, Hachioji, Japan

[73] Assignee: Olympus Optical Co., Ltd., Japan

[21] Appl. No.: 513,913

[22] Filed: Jul. 14, 1983

[30] Foreign Application Priority Data

Jul. 20, 1982 [JP] Japan ............................. 57-126276

[51] Int. Cl.$^4$ ............................................. G01D 9/28
[52] U.S. Cl. .................................. 364/558; 346/33 A
[58] Field of Search ....... 364/558; 346/33 A, 33 ME, 346/13; 356/344, 433, 443, 444

[56] References Cited

U.S. PATENT DOCUMENTS

| 3,706,877 | 12/1972 | Clifford, Jr. et al. | 364/558 |
| 3,842,422 | 10/1974 | VandenBroek et al. | 346/13 |
| 3,965,477 | 6/1976 | Hambleton et al. | 346/33 A |
| 4,005,434 | 1/1977 | Golias et al. | 364/558 |
| 4,429,996 | 2/1984 | Kamachi et al. | 356/344 |

Primary Examiner—Errol A. Krass
Assistant Examiner—Heather R. Herndon
Attorney, Agent, or Firm—Parkhurst & Oliff

[57] ABSTRACT

A method of recording a densitogram representing densities of albumin, $\alpha_1$-globulin, $\alpha_2$-globulin, $\beta$-globulin and $\gamma$-globulin in an electrophoresis is disclosed. In order to display the densitogram representing the change in density of the substances, an area of the densitogram surrounded by a densitogram curve and a base line is made proportional to a total density T which is measured separately by a colorimetric method. Successive density signals $X_n$ are adjusted by multiplying them with a density output ratio R which is derived in accordance with the following equation, $$R = \frac{K \cdot T}{\Sigma X_n \cdot Y \cdot P}$$

wherein K is a coefficient denoting an area on a record paper per unit density, $\Sigma X_n$ is an accumulated density signal, Y is a gain of a recorder and P is a recording pitch of the recorder.

4 Claims, 5 Drawing Figures

|  | Fraction % | Protein Density |
|---|---|---|
| Alb | 68 % | 4.76 g/dl |
| $\alpha_1$ | 3 % | 0.21 g/dl |
| $\alpha_2$ | 8 % | 0.56 g/dl |
| $\beta$ | 8 % | 0.56 g/dl |
| $\gamma$ | 13 % | 0.91 g/dl |

Total Protein Density 7 g/dl

|  | Fraction % | Protein Density |
|---|---|---|
| Alb | 51.5 % | 2.38 g/dl |
| $\alpha_1$ | 4.5 % | 0.21 g/dl |
| $\alpha_2$ | 12.1 % | 0.56 g/dl |
| $\beta$ | 12.1 % | 0.56 g/dl |
| $\gamma$ | 19.7 % | 0.91 g/dl |

Total Protein Density 4.26 g/dl

METHOD OF RECORDING DENSITOGRAM REPRESENTING DENSITIES OF FRACTIONATED SUBSTANCES

BACKGROUND OF THE INVENTION

The present invention relates to a method of recording a densitogram representing densities of fractionated substances contained in a sample.

For instance, in an electrophoretic apparatus for analyzing various proteins in a serum sample, there is formed a densitogram representing fraction curves of albumin (Alb), alpha-1-globulin ($\alpha_1$), alpha-2-globulin ($\alpha_2$), beta-globulin ($\beta$) and gamma-globulin ($\gamma$), fraction percentages of these protein substances, and a ratio (A/G) of albumin to total globulin. By means of such data, it is possible to know a relative change in density of the protein substances. Recently, in addition to such a relative change in density, an absolute change in density of the substances has become important. In order to satisfy such a request, absolute values of density of substances are obtained by deriving products of respective fraction percentages and a total density of the whole protein which is separately measured by the known refraction method or colorimetric method.

For instance, a protein composition of a patient shown in FIG. 1 is changed into that illustrated in FIG. 2 by any reason. It can be seen from FIGS. 1 and 2 that the fraction percentage of Alb is decreased by about 0.75 times and the fraction percentages of $\alpha_1$-, $\alpha_2$-, $\beta$- and $\gamma$-globulins are increased by 1.5 times. Then, the change in protein composition can be accurately known from the absolute protein density values which are obtained by multiplying respective fraction percentages with the total protein density.

However, in case of recording the densitogram, an automatic span control is utilized in such a manner that a peak value of the albumin fraction having usually the highest density is brought into a given constant level and the fractions of globulins are recorded relative to the albumin fraction. Then, densitograms shown by curves I and II in FIG. 3 are formed for the protein compositins illustrated in FIGS. 1 and 2, respectively. From these curves, the fractions of $\alpha_1$-, $\alpha_2$-, $\beta$- and $\gamma$-globulins seem to increase although the densities of these globulins are not changed at all and the density of albumin is decreased by two times.

It has also been known to record the densitogram without effecting the automatic span control. In this case, the densitogram can correctly represent the density change of the proteins as long as amounts of serum samples are equal to each other. However, in practice, it is very difficult to apply uniformly a given constant amount of samples to sample bearing films to be used in the electrophoresis. If amounts of samples applied to the bearing films are different from each other, the change in density of the proteins cannot be correctly known from the densitograms.

SUMMARY OF THE INVENTION

The present invention has for its object to provide a novel and useful method of recording densitograms representing accurately densities of a plurality of fractionated substances contained in samples, even if amounts of samples used for anaylsis are varied.

It is another object of the invention to provide a method of recording densitograms from which a user can visually know easily an accurate change in density of substances contained in a sample.

According to the invention, a method of recording a densitogram on a record medium with respect to a base line, said densitogram representing densities of fractionated substances contaied in a sample, comprises deriving density signals $X_n$ representing density values of the substances;

processing the density signals in such a manner that an area S surrounded by a densitogram curve to be formed and the base line is made equal to a product of a coefficient K denoting an area on the record medium per unit density and a total density T of whole substances; and supplying the processed density signals to a recorder to form a densitogram on the record medium.

DESCRIPTION OF THE PREFERRED EMBODIMENTS

Figures 1, 2, 3:
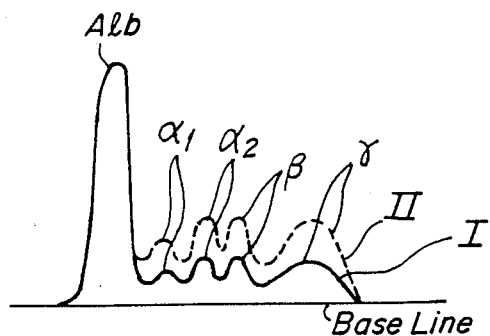
FIGS. 1 and 2 show an example of a change in a serum protein composition.
FIG. 3 is a graph showing densitograms recorded by a known method.
Figure 4:
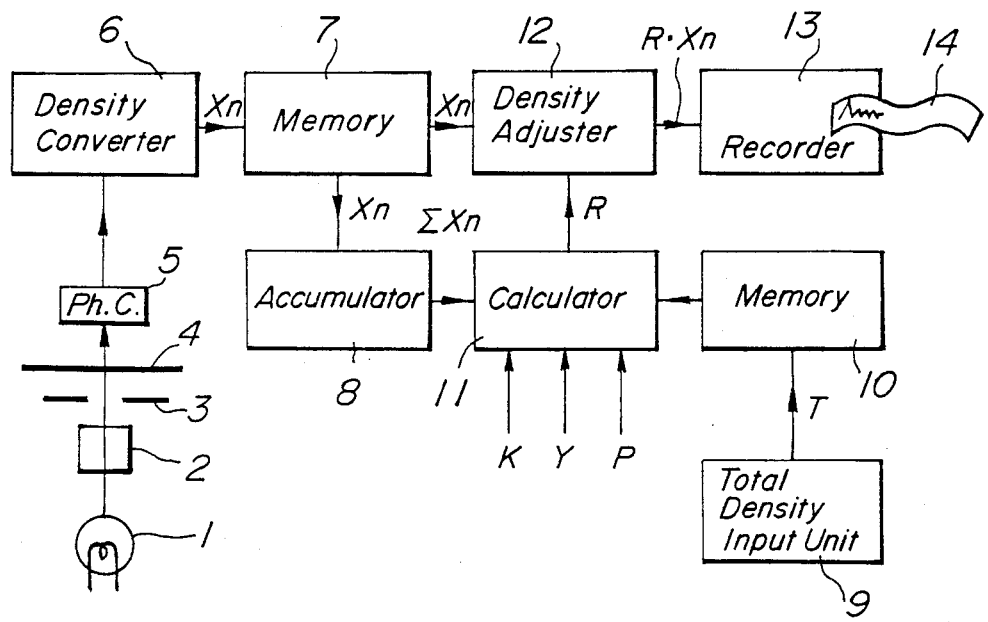
FIG. 4 is a block diagram illustrating an embodiment of an electrophoretic apparatus for performing the densitogram forming method according to the invention.

FIG. 4 is a block diagram showing an embodiment of an electrophoretic apparatus carrying out the densitogram forming method according to the invention. Light emitted from a light source 1 is collimated by an optical system 2 into parallel light which is then, via an interference filter (not shown) and a slit 3, made incident upon a film 4 bearing serum protein fractionated image. Light transmitted through the bearing film 4 is received by a photoelectric converting element 5. The light source 1, optical system 2, slit 3 and elemnt 5 are moved relative to the bearing film 4 in a direction in which the electrophoresis of protein substances in a serum sample has occurred to scan the fractionated image. An output signal from the photoelectric converting element 5 is sampled at a given sampling period and sampled values are successively converted by a density converting unit 6 into density signals $X_n$ (O.D) which are then stored in a density memory unit 7. At the same time, the density signals $X_n$ are accumulated in a density accumulator unit 8 to produce an accumulated density value $\Sigma X_n$. It should be noted that the density signals $X_n$ may be directly supplied to the density accumulator unit 8. Moreover, in order to derive a more accurate accumulated density value, use may be made of the Simpson's rule.

A total protein density T (g/dl) is separately measured by means of a colorimetric method or refraction method and the measured total protein density T is entered into a total protein density memory 10 via a total protein density input unit 9. The input unit 9 may be a keyboard or an interface connectable to a computer connected to the analyzer either in on-line or off-line. The total protein density T and the accumulated density value $\Sigma X_n$ are supplied to a calculator unit 11 to produce a ratio R which will be explained in detail hereinafter. The density signals $X_n$ stored in the memory unit 7 are successively read out and are supplied to a density output adjuster unit 12 in which amplitudes of the density signals are adjusted in accordance with the calculated value R. Then the adjusted output signals are suppled to a recorder 13 and a densitogram is recorded on a record medium such as an elongated record paper 14.

Now it is assumed that a coefficient representing an area on the record medium 14 per unit density is denoted by K ($cm^2/(g/dl)$), a ratio of the output amplitude per unit density at the density output adjuster unit 12 is represented by R (volt/O.D), a gain of the recorder 13 is denoted by Y (cm/volt) and a recording pitch of the densitogram at the recorder 13 is expressed by P (cm), then an area S ($cm^2$) surrounded by a curve of the densitogram and a base line can be represented by the following equation (1).

$$S = \Sigma X_n \cdot R \cdot Y \cdot P \qquad (1)$$

In order to satisfy the necessary condition S=KT according to the invention, the following equation (2) should be satisfied.

$$R = \frac{K \cdot T}{\Sigma X_n \cdot Y \cdot P} \qquad (2)$$

According to the present embodiment, in the calculator unit 11, there have been previously set the values K, Y and P as given constants. Then, the density output ratio R is calculated in accordance with the above equation (2). Then the calculated density output ratio R is supplied to the density output adjuster unit 12 in which products of the density signals $X_n$ and the ratio R are calculated as the adjusted or corrected density signals $R \cdot X_n$. The density values $R \cdot X_n$ thus adjusted are supplied to the recorder 13. In the recorder 13, the record paper 14 is fed at a speed corresponding to the recording pitch P and a recording pen is moved in a direction perpendicular to the paper feed direction by distances corresponding to the adjusted density values $R \cdot X_n$ to form the densitogram.

Figure 5:
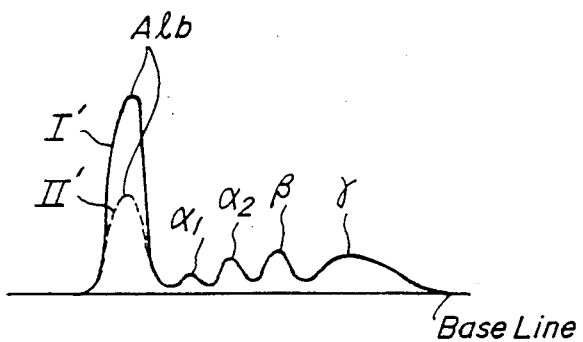
FIG. 5 is a graph depicting densitograms formed by the method according to the invention.

According to the invention, since the area of the densitogram surround by the curve and the base line is made in proportion to the total protein density, respective areas of each fraction correspond to respective density values as illustrated by curves I' and II' in FIG. 5. Therefore, the change in amounts of the protein substances can be visually judged in an easy and accurate manner.

It should be noted that the present invention is not limited to the above explained embodiment in which the densitogram of the serum protein fractions is formed, but may be equally applied to electrophoresis for isozyme and lipoproteins, and chromatography.

According to the invention, since the densitogram is so recorded that the area surrounded by the curve and the base line is made proportional to the toal density of the substances, the change in the fractions of the densitogram always corresponds to the change in density of substances contained in a sample, even if an amount of the sample applied to the sample bearing medium is varied. Therefore, the variation in density of substances can be visually and easily confirmed by the densitogram.

What is claimed is:
1. A method of recording a densitogram on a record medium with respect to a base line, said densitogram representing densities of a plurality of fractionated substances contained in a sample comprising the steps of:
deriving density signals $X_n$ representing density values of the fractionated substances;
processing the density signals in such a manner that an area S surround by a densitogram curve to be recorded on the record medium and the base line is made equal to a product of a coefficient K denoting an area on the record medium per unit density and a total density T of the pluarality of fractionated substances; and
supplying the processed density signals to a recorder to form a densitogram on the record medium.
2. A method according to claim 1, wherein said processing step comprises
storing the density signals in a memory means;
accumulating the successive density signals $X_n$ to produce an accumulated density value $\Sigma X_n$;
setting values of the coefficint K, a gain Y of the recorder and a recording pitch P of the recorder;
calculating a density output ratio R in accordance with an equation of

$$R = \frac{K \cdot T}{\Sigma X_n \cdot Y \cdot P} \; ; \text{ and}$$

deriving products of respective density signals $X_n$ and the density output ratio R to produce the processed density signals $R \cdot X_n$.
3. A method according to claim 2, wherein said accumulating step comprises accumulating the successive density signals read out of the memory means.
4. A method according to claim 2, wherein said total density T is stored in a memory unit and said calculation for the density output ratio R is effect by reading the total density T out of the memory unit.

* * * * *